(12) United States Patent
Voigt et al.

(10) Patent No.: US 12,259,537 B2
(45) Date of Patent: Mar. 25, 2025

(54) METHOD FOR OPERATING A MICROSCOPY SYSTEM, AND MICROSCOPY SYSTEM

(71) Applicant: Carl Zeiss Meditec AG, Jena (DE)

(72) Inventors: Christian Voigt, Abtsgmünd (DE); Markus Philipp, Aalen (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 18/117,377

(22) Filed: Mar. 3, 2023

(65) Prior Publication Data

US 2023/0204933 A1    Jun. 29, 2023

Related U.S. Application Data

(63) Continuation of application No. PCT/EP2021/074011, filed on Aug. 31, 2021.

(30) Foreign Application Priority Data

Sep. 3, 2020   (DE) .................. 10 2020 211 133.2

(51) Int. Cl.
*G02B 21/00*         (2006.01)
*G02B 21/02*         (2006.01)
(Continued)

(52) U.S. Cl.
CPC ..... *G02B 21/0012* (2013.01); *G02B 21/0044* (2013.01); *G02B 21/006* (2013.01); (Continued)

(58) Field of Classification Search
CPC ............ G02B 21/00; G02B 21/0004; G02B 21/0012; G02B 21/0016; G02B 21/0028;
(Continued)

(56) References Cited

U.S. PATENT DOCUMENTS 5,205,522 A    4/1993  Nakamura
5,748,366 A *  5/1998  Yasunaga ........... G02B 21/0012
                                                    359/368
(Continued)

FOREIGN PATENT DOCUMENTS

DE          10353961 A1    6/2005
DE      102014210046 A1   12/2015
(Continued)

OTHER PUBLICATIONS

Preliminary Report dated Dec. 3, 2021 of international application PCT/EP2021/074011 on which this application is based.
(Continued)

*Primary Examiner* — Thong Q Nguyen
(74) *Attorney, Agent, or Firm* — Ewers IP Law PLLC; Falk Ewers

(57) ABSTRACT

A method for operating a microscopy system and to a microscopy system are provided. A pivot point is defined, wherein the microscopy system is operated such that a microscope of the microscopy system moves at a constant distance around the pivot point, wherein a reference surface is determined, wherein an intersection of an optical axis of the microscope and the reference surface is determined as the pivot point, wherein the pose of the reference surface is defined in a focal position-independent reference coordinate system and the pivot point is determined as the intersection of the optical axis with the thus defined reference surface in the reference coordinate system.

12 Claims, 3 Drawing Sheets

(51) Int. Cl.
*G02B 21/24* (2006.01)
*G02B 21/36* (2006.01)

(52) U.S. Cl.
CPC ......... *G02B 21/008* (2013.01); *G02B 21/025* (2013.01); *G02B 21/24* (2013.01); *G02B 21/36* (2013.01)

(58) Field of Classification Search
CPC .................. G02B 21/0052; G02B 21/006; G02B 21/008; G02B 21/02; G02B 21/025
USPC .................................................. 359/368–398
See application file for complete search history.

(56) References Cited

U.S. PATENT DOCUMENTS

| | | | |
|---|---|---|---|
| 11,540,700 | B2 | 1/2023 | Nagao |
| 11,602,404 | B2 | 3/2023 | Arai et al. |
| 2003/0151810 | A1 | 8/2003 | Haisch et al. |
| 2004/0236352 | A1 | 11/2004 | Wang et al. |
| 2005/0117207 | A1 | 6/2005 | Haisch |
| 2005/0123289 | A1 | 6/2005 | Schweikard |
| 2006/0274444 | A1 | 12/2006 | Haisch |
| 2007/0083098 | A1 | 4/2007 | Stern et al. |
| 2012/0109377 | A1 | 5/2012 | Stern et al. |
| 2013/0231561 | A1 | 9/2013 | Marx et al. |
| 2014/0296870 | A1 | 10/2014 | Stern et al. |
| 2015/0346473 | A1 | 12/2015 | Emsperger et al. |
| 2017/0112368 | A1 | 4/2017 | Stern et al. |
| 2019/0060008 | A1 | 2/2019 | Bailey et al. |

FOREIGN PATENT DOCUMENTS

| | | |
|---|---|---|
| DE | 112017005655 T5 | 8/2019 |
| EP | 1333306 A2 | 8/2003 |
| EP | 1537830 A1 | 6/2005 |
| EP | 3175810 A1 | 6/2017 |
| JP | H05168648 A | 7/1993 |
| JP | H06324270 A | 11/1994 |
| JP | H08131457 A | 5/1996 |
| JP | 2003309861 A | 10/2003 |
| JP | 2003310638 A | 11/2003 |
| JP | 2016053699 A | 4/2016 |
| JP | 2018075121 A | 5/2018 |
| WO | 2015151447 A1 | 10/2015 |
| WO | 2018088203 A1 | 5/2018 |

OTHER PUBLICATIONS

Office Action issued in German Patent Application No. DE 10 2020 211 133.2, dated Apr. 28, 2021 (from which this application claims priority) and English language translation thereof.
Office Action dated Jul. 25, 2023, issued in Japanese counterpart application No. 2023-514840 and English-language Office Action Summary thereof.
Office Action dated Sep. 7, 2023, issued in Chinese counterpart application No. 202180054289.3 and English-language translation thereof.
Chinese Search Report dated Mar. 21, 2024, of Chinese counterpart application No. CN 2021800542893, and English language translations thereof.
International Preliminary Report on Patentability dated Aug. 4, 2022, in international application PCT/EP2021/074011 on which this application is based, and English-language translation thereof.

* cited by examiner

METHOD FOR OPERATING A MICROSCOPY SYSTEM, AND MICROSCOPY SYSTEM

CROSS REFERENCE TO RELATED APPLICATIONS

This application is a continuation application of international patent application PCT/EP2021/074011, filed Aug. 31, 2021, designating the United States, and claiming priority to German application 10 2020 211 133.2, filed Sep. 3, 2020, and the entire content of this application is incorporated herein by reference.

TECHNICAL FIELD

The disclosure relates to a method for operating a microscopy system and to a microscopy system.

BACKGROUND

Microscopes are often used to provide a magnified view of examination objects. In medical applications, so-called surgical microscopes are used in particular for assisting surgical interventions. They serve, among other things, to provide a magnified view of regions of a body, in order to give a surgeon better visual orientation during an intervention. These surgical microscopes are generally mounted in a movable manner, in particular on a stand. Among other things, this allows a user to change a pose, that is to say a position and/or orientation, of the microscope, for example in order to modify a viewing angle onto an examination region or in order to view other examination regions.

Regular repositioning may be required when using such microscopy systems. In this case, it is necessary to adjust up to seven degrees of freedom in order to obtain a desired view of the situs, specifically three translational degrees of freedom, three rotational degrees of freedom, and the adjustment of a variable working distance.

There are a number of solutions in the related art for the application of observing a specific working point from different perspectives. For example, EP 1 537 830 A1 describes a method and an apparatus for observing objects from different viewing directions using a microscope. Here, a first image of the target region of the object is created and saved, the microscope is pivoted through a defined angle, a second image is created and saved, and then one and the same part of the object is marked in both images. Furthermore, the coordinates of the part of the object are calculated by triangulation and the control of the microscope is configured in such a way that a pivoting movement around this point can be carried out.

Also known is US 2006/0274444A1, which describes a microscopy system including microscope optics having at least one lens and an optical axis of this lens, the optical axis intersecting with an object plane in a focal region, with a control device attempting to keep a position of the intersection constant during operation of the microscopy system. This document further discloses that a point outside the focal region can also be kept constant during operation of the microscopy system. Since, according to the teaching of this document, the object plane is located in the focal region, the pose of the object plane is focal position dependent.

A so-called point-lock function is also known. Here, the microscopy system is moved around a focal point. There are different variants in this context. In a first variant, the microscopy system or the microscope of the microscopy system is moved in position-controlled fashion along a spherical surface, for example by using a joystick, with the orientation of the microscope being simultaneously adjusted so that the optical axis intersects the focal point at all times. In a second variant, a user moves the microscope, with the orientation and focus being automatically updated so that the optical axis intersects the focal point.

When the point-lock function is activated, the user can manually change the focus, but the pivot point cannot be changed and, in particular, remains stationary at the location defined by the focal position during the activation.

In certain applications, it is desirable not to carry out a rotational movement of the microscopy system or the microscope around a point defined by the focal position, that is to say not to pivot around such a point, but instead to carry out a rotational movement around a point outside of the focal position. By way of example, in so-called keyhole operation scenarios, it may be desirable not to pivot about a point on a base surface of the cavity, since in this case relatively small rotational movements may already lead to the view through the microscope being obscured by the structures bounding the keyhole.

Current operating scenarios for setting a pivot point outside the focus plane are time-consuming and, in particular, require a large number of steps. By way of example, it is known to define such a pivot point outside of the focus plane by first focusing on a region at the edge of the keyhole level with the desired subsequent pivot point. The microscope is subsequently positioned in a desired pose, that is to say in a desired position and with a desired orientation, in particular in such a way that the optical axis runs through the area encompassed by the keyhole, and the previously explained point-lock mode is then activated. However, in order to view the situs, the focus of the microscope must then still be readjusted.

Disadvantages of this method include the need for a plurality of steps to be successively carried out in a coordinated manner, requiring a not very intuitive operation. Further, it is necessary to leave the point-lock mode activated in order not to lose the set pivot point. Each time repositioning is interrupted in the point-lock mode, even if the pivot point does not change, it is necessary to readjust the pivot point. To adjust the pivot point, it is further necessary to first set the focus on the edge of the keyhole, with it then being necessary to position the microscope in the desired pose before the point-lock mode is activated. Not only does this require additional time, but the view of the situs, which is particularly important in critical situations, is also interrupted during the repositioning. In such a method, contactless control, which can also be referred to as hands-free operation and is implemented, for example, by actuating a foot switch, is not possible either or only possible with difficulty.

In the related art, JP 2003 310638 A is also known, which describes surgical observation equipment and, in particular, the control of a support arm mechanism of a surgical observation means used during an operation.

EP 1 333 306 A2 describes a stereo microscopy method and a stereo microscopy system for generating at least one pair of representations of an object, for observation by at least one user.

WO 2018/088203 A1 describes a medical support apparatus.

US 2004/236352 A1 describes a system and a method for carrying out minimally invasive cardiac interventions.

DE 11 2017 005655 T5 describes a medical support arm and a medical system.

SUMMARY

A technical problem therefore arises of developing a method for operating a microscopy system and a microscopy system, which simplify an operation of the microscopy system.

The solution to the technical problem is provided by a method for operating a microscopy system microscopy system as described herein.

The method for operating a microscopy system includes defining a pivot point as an intersection between an optical axis of a microscope of the microscopy system and a reference surface, operating the microscopy system such that a microscope of the microscopy system moves around the pivot point, determining a pose of the reference surface in a focal position-independent reference coordinate system independently of a focal position of the microscope, storing information about the pose of the reference surface in a retrievable form in a memory, retrieving the stored information about the reference surface to determine the pivot point after a change in a pose of the optical axis of the microscope of the microscopy system, and wherein the pivot point is determined as the intersection between the optical axis in a current pose and the reference surface defined by the stored information.

A microscopy system is also provided, which includes a microscope, a stand for holding the microscope, the stand comprising at least one drive device for moving the microscope, and at least one control and evaluation device, the microscopy system being operable, in particular controllable by the control and evaluation device, in such a way that the microscope moves around the pivot point, with a reference surface being determined, an intersection of an optical axis of the microscope with the reference surface being used as the pivot point.

According to an aspect of the disclosure, the pose of the reference surface is defined in a focal position-independent reference coordinate system and the pivot point is determinable as the intersection of the optical axis with the thus defined reference surface in the reference coordinate system.

In particular, the microscopy system can include a memory device, for example a RAM- or ROM-based memory device, in which information about the pose of the reference surface in the reference coordinate system and optionally further reference surface-specific information such as the shape of the reference surface, for example, are retrievably stored. This information can be retrieved by the control and evaluation device, with the pivot point then also being able to be determined by this control and evaluation device.

Thus, the microscopy system is in particular configured in such a way that a method according to one of the exemplary embodiments disclosed in this disclosure can be carried out using the microscopy system. This advantageously results in a microscopy system with which such a method can be carried out.

In this case, the control and evaluation device may be embodied as or include a microcontroller or an integrated circuit. The control and evaluation device can in particular form the previously explained evaluation device for evaluating the topographical information. Further, the control and evaluation device can carry out the previously explained methods for determining/defining the reference surface.

In a further exemplary embodiment, the pose of the reference surface is defined in an object plane-independent reference coordinate system. This and corresponding advantages have already been explained above.

In a further exemplary embodiment, the microscopy system includes a device for generating topographical information, with said device, in particular, being able to be configured as an image capture device or being able to include at least one image capture device. This and corresponding advantages have already been explained above. Further alternatively or cumulatively, the microscopy system includes at least one pose detection device for detecting a pose of a pose marking instrument and/or of a marker.

Further, the microscopy system may include a device for detecting the viewing direction of a user. Further, the microscopy system may include a device for determining a pose of the microscope, in particular a viewing direction of the microscope or an orientation of the optical axis.

Likewise, the microscopy system may include a user input device. Further, the microscopy system may include an interface for reading in preoperative data.

BRIEF DESCRIPTION OF THE DRAWINGS

The disclosure will now be described with reference to the drawings wherein.

DESCRIPTION OF EXEMPLARY EMBODIMENTS

Identical reference signs hereinafter denote elements having identical or similar technical features.

Figure 1:
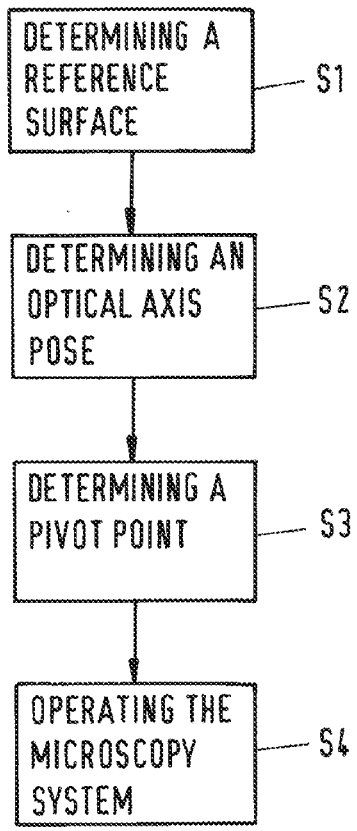
FIG. 1 shows a schematic flowchart of a method according to the disclosure.
Figure 4:
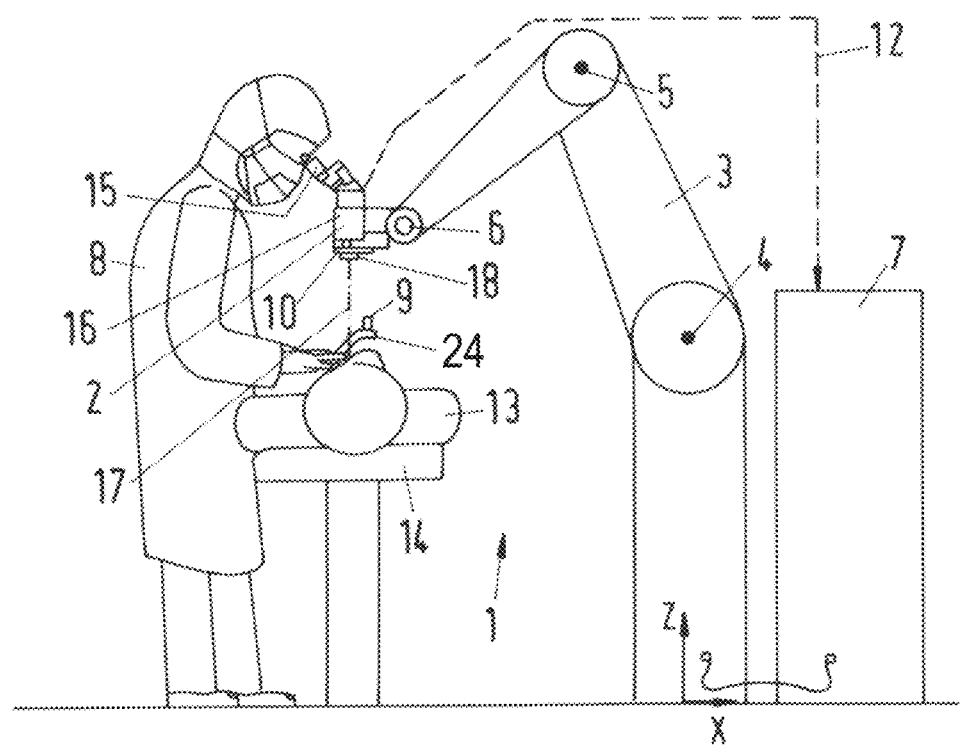
FIG. 4 shows a schematic view of a microscopy system according to an exemplary embodiment of the disclosure.

FIG. 1 shows a schematic flowchart of a method according to an exemplary embodiment of the disclosure for operating a microscopy system 1 (see FIG. 4, for example).

The microscopy system 1 includes a microscope 2. Within the meaning of this disclosure, a microscope designates a device for magnified visual representation of an examination object. The microscope can be a conventional light microscope, which generates an enlarged image representation by utilizing optical effects, in particular by means for beam guidance and/or beam shaping and/or beam deflection, for example lenses. However, the microscope can also be a digital microscope, wherein the image representation to be visualized by the microscope can be produced with an image capture device and can be displayed on an appropriate display device, for example a display unit.

The microscope can in particular include at least one eyepiece. The eyepiece refers to a part of the microscope through which or into which a user looks in order to view the image representation produced by the microscope.

Moreover, the microscope can include at least one objective. This objective can produce a real optical image representation of an examination object. Here, the objective may include optical elements for beam guidance and/or beam shaping and/or beam deflection.

The microscope may have an optical axis. This can be the optical axis of the objective. If the microscope includes a stereoscopic camera system, then the optical axes of the two image capture devices of the stereoscopic camera system intersect at the focal point. In this case, the optical axis of the microscope can correspond to the bisecting line between the optical axes of the two image capture devices, which also runs through the focal point.

Moreover, the microscope can include a microscope body. The microscope body may in this case include further optical elements for beam guidance and/or beam shaping and/or beam deflection. It is possible that the objective is releasably, that is to say also interchangeably, fastened on the microscope body. However, it is also possible that the objective is securely integrated in or on the microscope body. The objective can in this case be arranged in a fixed position relative to the microscope body.

Further, the microscopy system may include a stand for holding the microscope. The microscope, in particular the microscope body, can consequently be mechanically fastened to the stand. It is possible that the microscope is fastened to a free end of the stand, in particular in movable, for example pivotable, fashion. The stand is in this case embodied so as to allow a movement of the microscope in space, in particular in at least one degree of freedom, typically in six degrees of freedom. It is of course also possible for the stand to be embodied so as to allow a movement of the microscope in space in a restricted number of degrees of freedom, that is to say in particular in fewer than six degrees of freedom.

A degree of freedom in this instance can be a degree of translational or rotational freedom. In particular, a movement with three different degrees of translational freedom and three different degrees of rotational freedom can be enabled by the stand.

The degrees of freedom in this instance may relate to a global reference coordinate system. A vertical axis (z-axis) of this reference coordinate system may be oriented parallel to gravitational force and counter thereto. A longitudinal axis (x-axis) of the reference coordinate system and a transverse axis (y-axis) of the reference coordinate system may in this instance span a plane oriented perpendicular to the vertical axis. Moreover, the longitudinal axis and the transverse axis may also be oriented orthogonal to one another. Thus, the reference coordinate system may be a Cartesian coordinate system.

Moreover, the stand may include at least one drive device for moving the microscope. The stand typically includes multiple drive devices. A drive device in this instance refers to a device for producing a driving force or a drive moment. Such a drive device can be a servo motor, for example. Of course, the stand may also include means for transmitting forces/moments, for example gear units. In particular, it is possible for the at least one drive device to be controlled in such a way that the microscope carries out a desired movement and hence a desired change in pose in space or adopts a desired pose in space. In this instance, a pose refers to a position and/or an orientation. It is in this case possible that a speed of movement is limited to a predetermined maximum speed.

For example, the at least one drive device can be controlled in such a way that an optical axis of the objective adopts a desired orientation. Moreover, the at least one drive device can be controlled in such a way that a reference point of the microscope, for example a focal point, is positioned at a desired position in space.

A target pose in this instance can be specified by a user or by another superordinate system. Methods for controlling the at least one drive device on the basis of a target pose and a kinematic structure of the stand are known here to the person skilled in the art. The user in this instance can refer to a person who operates the microscope, in particular who looks into/through the eyepiece in order to obtain a magnified view of an object. It is possible that the microscope is what is known as a surgical microscope. In this case, the user can be a surgeon, in particular.

Further, a pivot point is defined and the microscopy system, in particular the at least one drive device and/or at least one braking device of the microscopy system, is operated so that the microscope of the microscopy system, explained above, moves around the defined pivot point, in particular but not necessarily at a constant distance. This pivot point can also be referred to as the pivot. In particular, the microscopy system can be operated in such a way that the microscope is moved around the defined pivot point, for example during a movement brought about by manual actuation. This can be achieved, for example, by virtue of an appropriate movement control, for example in the form of a force-controlled movement control, being implemented or caused by the operation. However, the microscopy system can also be operated in such a way that the drive device, explained above, is subject to such open-loop or closed-loop control that a movement of the microscope caused thereby is implemented accordingly, for example by a position control.

In this instance, a braking device can be embodied and/or arranged in such a way that the movement of the microscope about/along at least one axis is braked. The movement about/along a plurality of axes, but not all axes, can also be braked by the braking device. In a further alternative, the movement about/along all axes can be braked by the braking device.

The pivot point is determined as the intersection of the optical axis of the microscope and a reference surface. A pose of the optical axis can be determined to this end, as will be explained in more detail below.

According to an aspect of the disclosure, the pose of the reference surface is defined in focal position-independent fashion in a reference coordinate system. In other words, the pose of the reference surface is defined in a focal position-independent reference coordinate system. To this end, the pose can be defined accordingly, in particular in advance. Further, the pivot point is determined as the intersection of the optical axis with the thus defined reference surface in the reference coordinate system. The fact that the pose is defined independently of the focal position means that the pose of the reference surface does not change if the focal position changes, for example in the global reference coordinate system. Alternatively, but typically cumulatively, the pose of the reference surface can be defined in object plane-independent fashion in the reference coordinate system. In other words, the pose of the reference surface can be defined in an object plane-independent reference coordinate system. The fact that the pose is defined independently of the object plane means that the pose of the reference surface does not change if the object plane, in particular the pose thereof, changes, for example in the global reference coordinate system. The reference surface can in particular be a plane surface, that is to say a non-curved surface. However, it is also conceivable that the reference surface is not a flat surface, for example is a curved surface.

Consequently, the pose of the reference surface can be defined in a focal position-independent and object plane-independent reference coordinate system. It is possible that a definition in a focal position-independent reference coordinate system likewise is a definition in an object plane-independent reference coordinate system.

It is also possible for the pose of the reference surface to be defined in a sharpness plane-independent reference coordinate system, in particular alternatively or cumulatively to the definition in a focal position-independent and/or object plane-independent reference coordinate system. The fact that the pose is defined independently of the sharpness plane means that the pose of the reference surface does not change if the sharpness plane, in particular the pose thereof, changes, for example in the global reference coordinate system. The sharpness plane may denote a plane in the object space, with an object in said plane being imaged with a desired sharpness. Said plane may be oriented orthogonal to the optical axis of the microscope which intersects the sharpness plane at the center of the depth-of-field range. The depth-of-field range may be dependent in a known manner on a currently set focal length, the currently set distance, and also the currently set aperture. A working distance of the microscope may denote a distance between the sharpness plane and a final element of an objective system of the microscope along an optical axis of the microscope, which can be defined by the objective or objective system of the microscope. The working distance may also be a distance between the objective, in particular the final element, and the object at maximum focusing.

The working distance can be adjusted, for example by a user or by performing an autofocus function, in order to define the pose of the sharpness plane. If the working distance changes, the pose of the sharpness plane also changes. Hence, a change in the focal point, in particular in the pose thereof, can also cause a change in the pose of the sharpness plane. The object plane may correspond to the sharpness plane.

The pose of the reference surface in said reference coordinate system may be predetermined in this instance, with information about a pose and optionally further reference surface-specific properties such as the shape thereof being able to be retrievably stored in a memory device. In this case, it is therefore necessary to determine the pose of the reference surface in the reference coordinate system and optionally further properties once before the determination of the pivot point, in particular before the first determination of a pivot point, with this information then being retrieved and evaluated accordingly when the pivot point is (re) determined. Various exemplary embodiments of this determination are explained in more detail below.

The reference coordinate system can be a patient-fixed coordinate system or a body part-fixed coordinate system, for example a bone- or skull-fixed coordinate system. The coordinate system can also be the previously explained global reference coordinate system. As a further alternative, the reference coordinate system can be a microscopy system- or microscope-fixed coordinate system. By way of example, the reference coordinate system can be a coordinate system which is arranged stationarily relative to a base section of a stand of the microscopy system. Movable parts of the stand can be fastened to this base section. When used as intended, the base section can be arranged stationarily on a floor surface. This does not preclude the base section from being able to be moved along the floor surface, for example on rollers, for the purposes of transporting the microscopy system.

Consequently, the pivot point is determined in such a way that the pivot point does not change, in particular in the time following the definition of the pivot point, when a focal position of the microscope is changed. In other words, the pose of the defined pivot point does not change if the focal position of the microscope is changed after the pivot point has been defined. It is also possible that the pose of the defined pivot point does not change if the pose of the object plane and/or the sharpness plane of the microscope is changed after the pivot point has been defined.

In particular, the reference surface can be determined in such a way that it does not correspond to the focus plane or is not arranged completely in the focus plane of the microscope. However, it is conceivable that a part of the reference surface is arranged in or intersects the focus plane. Additionally, the reference surface can be determined in such a way that it does not correspond to the object plane and/or sharpness plane or is not arranged completely in this plane/these planes. However, it is conceivable that a part of the reference surface is arranged in or intersects this plane/these planes.

In this case, the focus plane denotes a plane in which the focal point is arranged, and which runs perpendicular to the optical axis. Thus, using the proposed method, it is possible to define not the focal point but instead a pivot point outside of the focus plane as the pivot point.

It is also possible to define the pivot point independently of the focal point. This can mean that the pivot point is defined in such a way that it does not change when the focal point changes.

In this case, the reference surface can be determined on the basis of data. This can mean that the reference surface is determined on the basis of data generated preoperatively or intraoperatively. Data generated intraoperatively can in particular be data which encode topographical information of the situs. Data generated intraoperatively can also be data generated by a pose detection device and encoding a spatial pose of a pose marking instrument or a marker. This will be explained in more detail below. The data can also encode operating parameters of the microscope.

The reference surface can also be determined on the basis of data from a user input.

Defining the pivot point as the intersection of the optical axis with a reference surface advantageously results in a simple, accurate, and reliable definition of the pivot point. Furthermore, ensuring a simple, accurate, and reliable definition of a pivot point outside of the focus plane can advantageously be achieved. This in turn advantageously improves the operation of the microscopy system, in particular in the keyhole operation scenario explained above, with the pivot point being able to be defined as a point in the area encompassed by a situs opening, for example, as explained in more detail below. In comparison with previous methods, this yields a simple and hence time-saving operation of the microscopy system, particularly in such an operation scenario.

Advantageously, the reference surface for determining the pivot point only has to be defined once and can then be stored in a retrievable form. According to an aspect of the disclosure, stored information about the reference surface is then retrieved at a later point in time, and a new pivot point is determined as the intersection of the optical axis in its current pose with the stored reference surface. Then, the at least one drive device and/or at least one braking device of the microscopy system can be operated in such a way that the explained microscope of the microscopy system moves around the newly defined pivot point. This enables a repeated movement of the microscope around a pivot point on the reference surface, which can also be referred to as pivoting, without a renewed determination and definition of the reference surface being made possible. This allows a user to repeatedly activate a pivot mode, with the rotational movement then always being performed around a pivot point in the stored reference surface.

In a further exemplary embodiment, the pose of the reference surface is defined in an object plane-independent reference coordinate system. This and corresponding advantages have already been explained above.

In a further exemplary embodiment, the pose and/or the shape of the reference surface is defined in such a way that the area encompassed by a situs opening forms the reference surface or is encompassed by the reference surface.

The situs opening can be defined by anatomical structures. In particular, the situs opening can be a cranial opening, with this opening being defined by the skull surrounding the opening. It is also conceivable that the situs opening is defined by medical instruments, for example a trocar, or by medical clamps.

In this instance, the area encompassed by the situs opening can denote an area which is bounded by an edge of the situs opening in a cross-sectional plane, with this cross-sectional plane being oriented perpendicular to a central center line of the situs opening. In other words, the area in the aforementioned cross-sectional plane is bounded by the edge of the situs opening.

A shape and/or size of the encompassed area may change for different cross-sectional planes along the central center line. In this case, the encompassed area can be determined, for example, as the area with the minimum size from the set of areas arising for different cross-sectional planes.

What advantageously arises as a result is that a pivot point for the microscopy system can be easily, quickly, accurately, and reliably defined independently of the focus plane, in particular outside of the focus plane, in such a way that, during an operation of the microscopy system with this defined pivot point, that is to say in a point-lock mode activated by this pivot point, a user can reliably look through the situs opening without the view being obscured when the focus is changed. A simplified definition of the pivot point is also made possible. This is advantageous in the already explained keyhole operation scenarios, in particular.

In a further exemplary embodiment, the situs opening, in particular the shape and/or pose thereof, is defined automatically. For this purpose, output signals, in particular, from detection devices, in particular sensors, can be evaluated. Exemplary methods in this respect are explained in even greater detail below. It is also possible to define the situs opening by evaluating data, in particular image data, generated preoperatively or intraoperatively.

Alternatively, the situs opening is defined manually, in particular by a user input.

Naturally, it is also possible for the situs opening to be defined semi-automatically, with an automatic definition algorithm being assisted by user inputs.

In this case, data for determining the reference surface are generated, for example, by detection devices or by a user input.

This advantageously results in a simple and reliable definition of the situs opening and hence of the reference surface.

In a further exemplary embodiment, the reference surface is a bounded surface. It is possible that the reference surface is a surface that is bounded on all sides. In this case, the reference surface can be a circular surface or an oval surface, for example. Naturally, it is also conceivable for the reference surface to have different shapes, in particular also a free-form shape.

Alternatively, it is possible that the reference surface is a surface that is not bounded on all sides. By way of example, the reference surface can be a surface bounded only on one side. In this case, it may be possible that at least a section of an edge of the reference surface is part circular or part oval. Naturally, it is also conceivable for the section of the edge to have different shapes, in particular also a free-form shape.

The use of a reference surface as a bounded surface advantageously results in the fact that the pivot point can be reliably defined in a desired region, as a result of which it is possible to ensure, for example, that the user can reliably look through the situs opening when the microscopy system is operated with the pivot point defined in this way, in particular if the reference surface corresponds to the area encompassed by the situs opening.

Naturally, it is also conceivable that the reference surface is an unbounded surface, that is to say a plane. In this case, a particularly simple definition of the pivot point is obtained in an advantageous way.

In a further exemplary embodiment, the reference surface is a curved surface. This advantageously results in a further improvement in the reliability of the definition of the pivot point, which in turn, as already explained above, reduces the risk of the user losing sight when operating with this defined pivot point.

In a further exemplary embodiment, the pose and/or the shape of the reference surface is determined on the basis of preoperatively generated data. Such preoperatively generated data can be, for example, CT-based data or MRI-based data. Naturally, it is also possible to use other methods to generate data preoperatively, which encode the pose and/or the shape of the reference surface or on the basis of which the pose and/or the shape of the reference surface can be defined.

By way of example, when planning an operation, the pose and/or the shape of a situs opening can be defined on the basis of preoperatively generated data, in particular data that represent the anatomy of the patient to be operated on.

In this case, it may be necessary to bring the preoperative data into a geometric relationship with the explained reference coordinate system. This can be implemented, for example, by a registration process known to those skilled in the art. In particular, this enables the determination of a transformation rule for the transformation of the pose and/or shape, determined on the basis of the preoperatively generated data, from the coordinate system of the preoperative data into the reference coordinate system. This can be used to determine the pose and/or the shape of the reference surface on the basis of the preoperatively generated data.

This advantageously results in a simple determination of the pose and/or the shape of the reference surface.

In a further exemplary embodiment, topographical information of the situs is determined, the pose and/or shape of the reference surface being determined on the basis of this information. The data used to determine the reference surface can encode the topographical information, or a part thereof, in this instance.

The topographical information can be generated by a device for generating topographical information. Such a device can include an image capture device, in particular. In this case, the pose and/or the shape of the reference surface can therefore be determined in image-based fashion. To this end, image representations generated by at least one image capture device can be evaluated. In this context, an image capture device can denote a device for determining topographical information of the situs. An image capture device can generate a two-dimensional or three-dimensional image representation and can be a CCD camera or a CMOS camera, for example. However, an image capture device can also be a time-of-flight camera. The evaluation can be implemented by an evaluation device, which can be designed as, or include, a microcontroller or an integrated circuit.

In particular, at least one image, typically a plurality of images, generated by the microscopy system can be evaluated to this end. In this case, the microscopy system may include at least one image capture device, the image representations of which are evaluated, in particular by an evaluation device of the microscopy system, in order to determine the pose and/or the shape of the reference surface.

The image capture device of the microscopy system can be, in particular, the image capture device that serves to digitize the image representation generated by the microscope, with said image representation then being presented, for example, on an appropriate display device of the microscopy system.

Alternatively, it is also possible to evaluate image representations from an image capture device which is not part of the microscopy system and/or does not serve for the explained digitization. By way of example, the image capture device can be an image capture device of a pose detection device. The pose detection device can be a pose detection device of the microscopy system. In this case, for example, the image capture device can be arranged/attached to the microscopy system, but it is not used to digitize the image representation generated by the microscope.

Methods of image processing known to the person skilled in the art, for example segmentation methods, can be used for the image-based determination of the pose and/or the shape.

Like in the case of using preoperative data, it may be necessary to determine a geometric relationship between a coordinate system of the image capture device and the previously explained reference coordinate system by way of a registration, with the shape and/or the pose then being able to be determined on the basis of this geometric relationship, for example in the form of a coordinate transformation.

It is possible, for example, for a situs opening to be detected in one or more image representations, for example by making use of a suitable segmentation method. The area encompassed by the edge of the situs opening can then be defined as the reference surface.

It is also possible for the pose and/or shape of the reference surface to be determined on the basis of topographical information and additionally on the basis of a viewing direction of the microscope and/or a viewing direction of a user.

To this end, a viewing direction of the microscope can be determined. By way of example, this can be determined on the basis of the alignment of the microscope. By way of example, the viewing direction can be determined as the direction/orientation of the optical axis, in particular in the reference coordinate system.

The user's viewing direction can correspond to the viewing direction of the microscope. Alternatively, the user's viewing direction can be determined by a viewing direction detection device, for example a gaze tracking system known to those skilled in the art.

By way of example, it is possible to determine an intersection between the viewing direction and a surface of the situs that is determinable on the basis of the topographical information. The reference surface can then be defined in such a way that this intersection is arranged on the reference surface. Additionally, a search area for a situs opening can then be determined on the basis of the pose of this intersection, with a situs opening then being searched for using suitable methods for evaluating topographical information, for example for image processing. If a plurality of situs openings are detected, the area encompassed by the edge of the situs opening closest to the intersection can be defined as the reference surface. It is also possible for a user to align the viewing direction of the microscope or their viewing direction with the edge of the reference surface and change said viewing direction over a predetermined time interval so that said viewing direction is moved along the edge, thus defining the boundary of the reference surface.

It is also possible for the pose and/or shape of the reference surface to be determined on the basis of topographical information and further additionally on the basis of a pose of a pose marking instrument and/or marker. A pose marking instrument and a marker are explained in more detail below.

In this case, the pose and/or shape can be detected by evaluating the topographical information, that is to say in particular in image-based fashion.

Furthermore, at least one marker can be arranged in such a way that the pose and/or shape of the reference surface can be determined on the basis of the pose of the marker. By way of example, three or more than three markers can be arranged in such a way that their positions are located in a common plane, with the reference surface also being arranged in this plane.

Connecting lines between markers can encode a boundary line of the reference surface. The orientation of a marker can also encode an orientation of the reference surface. It is thus also possible for the pose of the reference surface to be defined by the pose of an individual marker.

Additionally, a search area for a situs opening can be determined on the basis of the pose of the instrument/marker, with a situs opening then being searched for using suitable methods for evaluating topographical information, for example for image processing. If a plurality of situs openings are detected, the area encompassed by the edge of the situs opening closest to the pose of the instrument/marker can be defined as the reference surface.

This likewise advantageously results in a simple and reliable determination of the shape and/or the pose of the reference surface.

In an exemplary embodiment, the reference surface is determined by defining at least one reference surface point, with the reference surface being defined as or being arranged in the plane which is oriented perpendicular to the optical axis of the microscope and in which the reference surface point is arranged. In this case, the data used for the determination can comprise, or encode information about, the pose of the reference surface point and the orientation of the optical axis.

To this end, it may be necessary to determine an orientation of the optical axis of the microscope, in particular in the previously explained reference coordinate system. Further, it may be necessary to define the pose of the reference surface point, typically likewise in the previously explained reference coordinate system. Exemplary methods for defining the pose of the reference surface point are explained below.

In this case, the reference surface point does not or does not necessarily correspond to the pivot point explained above.

This advantageously results in a simple and fast definition of the reference surface.

If the reference surface is determined in this way, the reference surface point may be defined only once and may be stored in a retrievable form, for example. Stored information about the reference surface point can then be retrieved and the reference surface can be determined on the basis of the reference surface point at a later point in time, with a new pivot point being determined as the intersection of the optical axis in its current pose with the reference surface determined thus. Then, the at least one drive device and/or at least one braking device of the microscopy system can be operated in such a way that the explained microscope of the microscopy system moves around the newly defined pivot point. This enables a repeated movement of the microscope around a pivot point on the reference surface, which can also be referred to as pivoting, without a renewed definition of the reference surface point being made possible.

Especially in this exemplary embodiment, but not exclusively, the reference surface can have a predetermined geometric shape, for example a circular shape or an oval shape, with properties of the geometric shape being able to be predetermined.

In a further exemplary embodiment, the at least one reference surface point is determined as a focal point set by a user. In this case, data for determining the reference surface can therefore additionally include operating parameter data of the microscope.

In this case, after the reference surface point has been determined/defined, the focal position of the microscopy system can be changed again, with, however, the reference surface being determined on the basis of the reference surface point that was set before the change. If a pose of the reference surface or reference surface point is not changed during an operation or an operation phase, the reference surface point only has to be defined once. Changes in the pose of the reference surface or reference surface point can emerge, for example, from changes in the pose of the patient.

If a change in the pose of the reference surface or reference surface point is determinable during an operation or an operation phase, for example by way of a suitable pose tracking system, then the pose of the reference surface or reference surface point can also be updated in accordance with the determined change in pose.

Alternatively, the at least one reference surface point is defined by the positioning of a pose marking instrument. The pose marking instrument can in particular be an instrument that can be manually positioned by a user, in particular during an operation. It is possible, for example, to define the reference surface point by virtue of the pose marking instrument being positioned by a user in a pose corresponding to the desired pose of the reference surface point, with a pose determination signal then being generated, for example by a user. This signal can be generated in particular by a user input, for example a haptic, an acoustic or any other type of user input. The pose of the reference surface point can be defined as the then determined pose of the pose marking instrument. The pose of the pose marking instrument can, for example, correspond to the pose of a predetermined point, for example the tip, of the pose marking instrument.

Alternatively, the reference surface point can be determined on the basis of a pose of at least one marker. Especially during an operation, a marker can be a statically arranged instrument, more particularly arranged at the situs.

To this end, a pose of the pose marking instrument or of the marker can be determined, in particular in the previously explained reference coordinate system. The pose can be determined, for example, by a pose detection device, for example an optical pose detection device, in particular a stereoscopic pose detection device. Naturally, other pose detection devices can also be used.

The pose of the pose marking instrument or of the marker can also be determined in image-based fashion, for example on the basis of image representations from an optical pose detection device or from image representations of an image capture device of the microscopy system.

The pose marking instrument or the marker can further include at least one target, for example, the latter including or having at least one marker element. In this case, a marker element can be, in particular, optically capturable and thus also detectable in an image representation, in particular can have an optically detectable pattern.

In this case, the target can be fastened to the pose marking instrument or the marker, for example.

A pose marking instrument can be designed, for example, as a syringe, tweezers, spoon, scissors, scalpel, forceps, aspirator or cautery, or other instrument that is dynamically positioned or able to be dynamically positioned by a user during an operation.

A marker can be configured, for example, as a clamp, in particular a skin clamp, holder, trocar, surgical retractor, skin stapler, but also a retractor, for example a brain retractor, or another instrument that is statically arranged during an operation.

The pose marking instrument or the marker can thus be formed by one of the instruments explained above.

In this case, data for determining the reference surface can therefore be data generated by a pose detection device.

As a result of this, a simple definition of the reference surface point likewise emerges in an advantageous manner.

Alternatively, the at least one reference surface point can be defined on the basis of a viewing direction detection. The viewing direction detection has already been explained above.

Further, the reference surface point can be defined as a point along the viewing direction, for example as the intersection of the viewing direction axis with a predetermined or user-defined topographical feature. This definition can be implemented by a user input, in particular an acoustic user input in the form of a voice command.

By way of example, an autofocus function can be implemented, with the reference surface point then being defined as the focal point determined after the autofocus function has been implemented. In this case, after the reference surface point has been determined/defined, the focus position of the microscopy system can be changed again.

As a result of this, a simple definition of the reference surface point likewise emerges in an advantageous manner.

In a further exemplary embodiment, the pose of a reference surface point is defined by changing the pose of a reference surface point that has already been defined. By way of example, the pose can be changed by determining a distance, with the pose of the reference surface point being determined by the pose of the reference surface point already defined being changed by the distance determined in this way, in particular along a predetermined direction, for example along a normal direction to the already defined reference surface or along the optical axis, in particular toward the microscope.

The distance can be defined for example by a user input, for example a haptic, an acoustic or any other type of user input. This advantageously results in a simple change in the reference surface point and hence also in the reference surface.

At least three reference surface points are determined in a further embodiment, the pose and/or the shape of the reference surface being determined in such a way that the at least three reference surface points are located on the reference surface or a distance of the reference surface points from the reference surface or a plane containing the reference surface is minimal. It is conceivable, for example, that the pose and/or the shape of the reference surface is determined in such a way that the at least three reference surface points form edge points of the reference surface. However, this is not mandatory. Thus, it is also conceivable that the at least three reference surface points do not form any edge points of the reference surface. With regard to the definition of a reference surface point, reference is made to the exemplary methods explained above. As a result of this, a simple definition of the reference surface likewise emerges in an advantageous manner.

In a further exemplary embodiment, the focal point is defined as the pivot point if the optical axis does not intersect the bounded reference surface. This advantageously means that a user can easily put the microscopy system both into the previously explained point-lock mode and into a mode for implementing a movement around a point defined in accordance with the proposed method.

It is possible for the microscopy system to be operated in such a way that a microscope of the microscopy system moves at a constant distance around the pivot point. Such a movement at a constant distance is of particular interest if a movement of the microscope is controlled with a manually operable control device, for example a joystick, wherein the change in the distance by operating the control device is undesirable or not possible. The constant distance allows a microscope movement, wherein the optical properties such as magnification, image section, brightness and optionally further properties remain the same or do not need to be changed during the movement. Naturally, this can also be ensured if the constant distance is ensured during a movement brought about by manual actuation.

In a further exemplary embodiment, a focal position is changed on the basis of the change in the distance of the microscope from the pivot point, that is to say in particular if the distance changes when the microscope moves around the pivot point. This can be implemented in automated fashion. The distance can be a distance along the optical axis of the microscope. By way of example, the change in focal position can be equal to the change in distance. In other words, refocusing can be carried out so that a focused point/region remains in focus even if the distance changes. In this case, the focal position can remain constant in the reference coordinate system even when moving around the pivot point.

However, the implementation of such refocusing is not mandatory. Thus, it may be desirable that the focal position is not changed (automatically) on the basis of the change in the distance of the microscope from the pivot point. In this case, the focal position can change in the reference coordinate system when moving around the pivot point.

Reference is now made to FIG. 1, which shows a schematic flowchart in which in a first step S1, a reference surface 19 is determined (see FIG. 3, for example). This includes, in particular, the determination of a pose, that is to say, for example, a position of a support point of the reference surface 19 and an orientation of the reference surface 19, in the reference coordinate system.

In this case, the reference surface 19 is determined on the basis of data. By way of example, preoperative data can be read in for the determination, with the reference surface 19 being determined by evaluating the preoperative data. To this end, it may be necessary to transform a coordinate system of the preoperative data into the previously explained reference coordinate system. This can be implemented using appropriate registration procedures.

By way of example, it is possible to use image processing methods to detect a situs opening 20 in the preoperative data, with this situs opening 20 being, for example, a planned situs opening 20 defined by an operation planner, for example by way of a user input.

The reference surface 19 can then be defined in such a way that the area encompassed by the detected situs opening 20 forms the reference surface 19 or is encompassed by the reference surface 19.

It is also possible to determine topographical information of the situs, in particular intraoperatively, with the data encoding the topographical information then being able to be evaluated in order to define the reference surface 19. As already explained in detail above, topographical information can be, for example, image information, for example in the form of 2-dimensional or three-dimensional image representations of the situs, with image information being able to be generated by one or more image capture device(s). By way of example, it is possible to use image processing methods to detect a situs opening 20 in this intraoperatively generated image data. In that case, too, the reference surface 19 can be defined in such a way that the area encompassed by the detected situs opening 20 forms the reference surface 19 or is encompassed by the reference surface 19.

Further, the determination of the reference surface 19 may also include the determination of the shape of the reference surface 19. This determination of the shape can in particular also be implemented by evaluating the explained data, for example by using suitable image processing methods. Naturally, however, it is also conceivable that the shape of the reference surface 19 is a predetermined shape. In this case, it may be possible that all properties of the shape are predetermined. It may also be possible that only certain properties of the shape are predetermined, while further properties of the shape are determined on the basis of data. By way of example, the shape of the reference surface 19 may be defined to be circular, with the radius being determined on the basis of data.

Further, the pose of the reference surface 19 determined in this way is retrievably stored in a focal position-independent reference coordinate system, in particular in the reference coordinate system shown in FIG. 4. In this case, the pose of the reference surface may also be defined in an object plane-independent and/or sharpness plane-independent reference coordinate system and be retrievably stored.

The reference surface 19 therefore need only be determined once, especially if a pose of a situs of the patient 13 (see FIG. 4) does not change. New pivot points can then be determined, in particular after a change in the pose of the optical axis 17, in each case as an intersection between the stored reference surface 19 and this optical axis 17 in the current pose thereof, that is to say in the current position and current orientation thereof.

Thus, if the pose of the reference surface 19 has already been determined, the stored information about the pose of the reference surface 19 can also be retrieved from a memory device as an alternative to the determination explained in the first step S1.

Further, a pose of an optical axis 17 of a microscope 2 is determined in a second step S2. This includes, in particular, the determination of the orientation of the optical axis 17 and the position of a support point of the optical axis 17, for example an intersection of the optical axis 17 with a lens of the microscope 2, in a reference coordinate system. The reference coordinate system is explained in more detail below with reference to FIG. 4. The orientation of the optical axis 17 can be determined, in particular, on the basis of output signals from pose/angle sensors of the microscopy system 1, in particular of a stand 3 of the microscopy system 1.

Further, a pivot point 21 for the microscope 2 is determined in a third step S3 as the intersection between the optical axis 17 and the reference surface 19. In particular, this includes the determination of the coordinates of this pivot point 21 in the reference coordinate system.

In a fourth step S4, drive devices and/or braking devices of a stand 3 (see FIG. 4, for example) of the microscopy system 1 are operated in such a way that the microscope 2 of the microscopy system 1 moves at a distance A (see FIG. 3, for example) around the pivot point 21. In this case, the distance A can be a constant distance. However, this is not mandatory. By way of example, movements of movable parts of the stand 3 about the axis of rotation 4, 5, 6 can be blocked to this end if the distance A would change as a result of these movements. Further, it is possible that only such movements with which the microscope 2 is moved at a constant distance A around the pivot point 21 are enabled or generated by the drive devices.

This operation can be subject to open-loop/closed-loop control by a control device 7. The control device 7 can also implement the determination of the pose of the optical axis 17, the determination of the reference surface 19, and the determination of the intersection.

Figure 2:
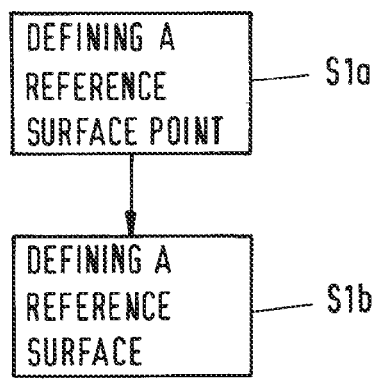
FIG. 2 shows a schematic flowchart for the determination of a reference surface.

FIG. 2 shows a schematic flowchart for the determination of the reference surface 19. Here, a reference surface point 22 (see FIG. 3B, for example) is defined in a first partial step S1a. This reference surface point 22 can differ from the pivot point 21 to be determined. Various options for defining a reference surface point 22 have been explained above. By way of example, the reference surface point 22 can be determined as a focal point of the microscope 2 set by a user, with the focal point being able to be changed again hereafter. It is likewise possible for the reference surface point 22 to be determined on the basis of a pose of at least one marker, with this pose being able to be determined in image-based fashion, for example. Further, it is possible for the reference surface point 22 to be defined on the basis of a viewing direction detection. Information about the reference point can be stored in retrievable form and allows a simple re-determination of the reference surface 19 and the pivot point 21.

In a further partial step 1b, the reference surface 19 is defined as a plane or determined as an area in the plane which is oriented perpendicular to the optical axis 17 of the microscope 2 and in which the reference surface point 22 is arranged.

It is possible that a plurality of reference surface points 22, in particular at least three reference surface points, are determined in the first partial step 1a, the pose and/or the pose of the reference surface 19 then being determined in such a way that the plurality of reference surface points 22 are located on the reference surface 19 or are spaced apart from the reference surface 19 or a plane containing the reference surface 19 by no more than a predetermined measure.

Figure 3A:
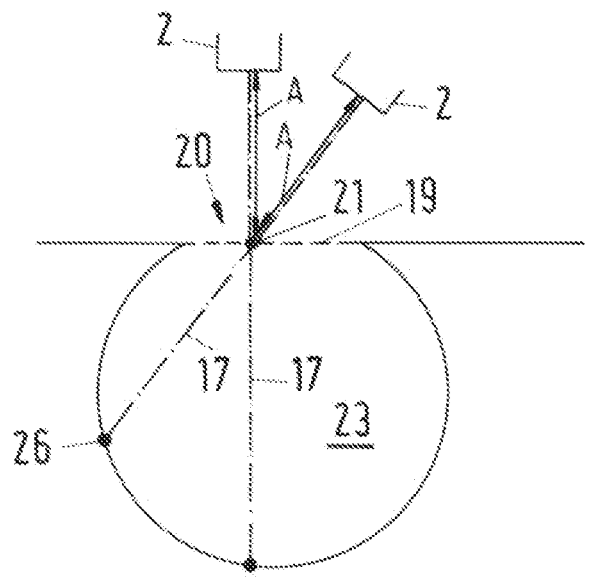
FIG. 3A shows a schematic view of a situs opening in a situs.

FIG. 3A shows a schematic view of a situs opening 20 in a situs. Also shown is a microscope 2 and an optical axis 17 of the microscope 2. Here, the microscope 2 is shown in different orientations. It is further evident that a pivot point 21 is arranged on a reference surface 19, with the pose and the shape of the reference surface 19 being defined in such a way that the area encompassed by the situs opening 20 forms the reference surface 19.

The situs opening 20 can be, for example, a cranial opening that is introduced into a patient's skull during a neurosurgical operation in order to gain access to underlying structures. A cavity 23 is regularly created in the brain, the diameter of which is larger than the diameter of the cranial opening. Defining the pivot point 21 as the point of the explained reference surface 19 advantageously means that a base surface of the cavity can be viewed from different viewing directions through the microscope 2 by a user, for example the neurosurgeon, without the view being obscured, for example by the cranial structure which includes the cranial opening, with the realization of this additionally being enabled by way of a movement with components in only a few degrees of freedom. It is also possible to set a focal point 26 of the microscope 2 independently of the pivot point 21. In particular, it is therefore possible to change a position of the focal point 26 without the position of the pivot point 21 being changed.

Figure 3B:
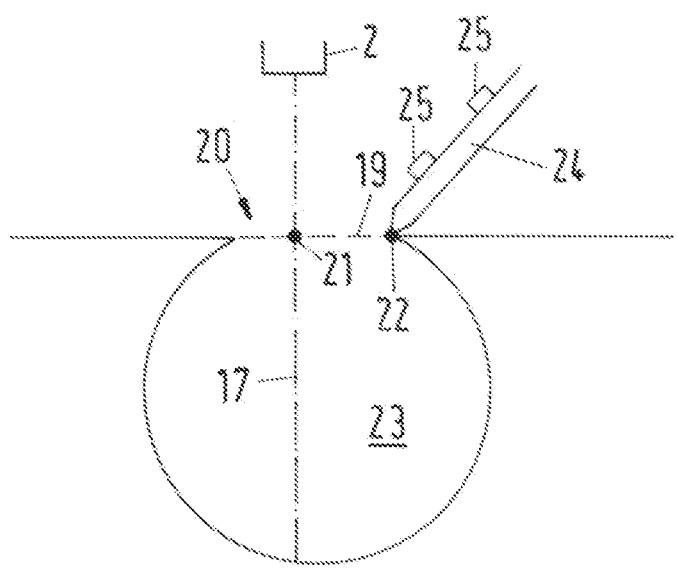
FIG. 3B shows a further schematic view of a situs opening in a situs.

FIG. 3B shows a further schematic view of a situs opening 20 in a situs. Likewise shown is a microscope 2 and an optical axis 17 of the microscope 2. It is further evident that a pivot point 21 is arranged on a reference surface 19, with the pose and the shape of the reference surface 19 being defined in such a way that the area encompassed by the situs opening 20 forms the reference surface 19.

Also shown is a pose marking instrument 24 which can be positioned by a user, for example. A pose of the pose marking instrument 24 that can be detected by a pose detection device (not shown), for example, is defined by a tip of the pose marking instrument 24. Optically detectable marker elements 25 are shown schematically, which marker elements can be detected by the pose detection device, with the pose defined by the tip then being able to be determined on the basis of these imaged marker elements 25. The marker elements 25 can be part of a target 9 (see FIG. 4). Also shown is that the reference surface point 22 is defined by the pose marking instrument 24. Said reference surface point defines the reference surface 19, which is simultaneously oriented orthogonal to the optical axis 17 of the microscope 2.

FIG. 4 shows a schematic view of a microscopy system 1 according to an exemplary embodiment of the disclosure. The microscopy system 1 includes a microscope 2, which is arranged on a stand 3 for holding the microscope 2, in particular at a free end of the stand 3. The stand 3 allows a movement of the microscope 2 in order to change the pose, that is to say the position and/or orientation, of the microscope 2. A reference coordinate system is depicted with a vertical axis z and a longitudinal axis x. The vertical axis z is here parallel to the direction of a gravitational force and is oriented counter to the latter. The longitudinal axis x is oriented perpendicular to the vertical axis z. A transverse axis (not shown) of the reference coordinate system is here oriented perpendicular to the longitudinal and vertical axes x, z, wherein the axes x, z form a Cartesian coordinate system.

The stand 3 shown is an example of a kinematic structure for holding and moving the microscope 2. A person skilled in the art will of course know that other kinematic structures may also be used.

The stand 3 includes drive devices (not shown) for moving the microscope 2. Here, the drive devices can, for example, allow a rotational movement of movable parts of the stand 3 about axes of rotation 4, 5, 6 and an axis of rotation parallel to the vertical axis z. Also shown is a control device 7, which is used to control the drive devices (not shown) and which may comprise a microcontroller, for example. In this case, the control device 7 can form a control and evaluation device.

Further, the control device 7 can also control braking devices (not shown) of the stand 3, which can brake or prevent the rotational movement of the movable parts.

With the control device 7, the drive devices can be controlled in particular in such a way that the microscope 2 implements a desired movement, in particular in the reference coordinate system. By way of example, it is possible to position the microscope 2 in a desired spatial position with a desired orientation. Further, the control device 7 can also serve to adjust operating parameters and/or movement parameters of the microscope 2, for example to adjust a focus value of the microscope 2. To this end, the control device 7 can be signal-connected and/or data-connected to the microscope 2 and/or to the drive devices.

The microscopy system 1 moreover includes a pose detection device for detecting a pose of an instrument 24 that can be held and moved by a user 8. The instrument 24 can in particular be a pose marking instrument 24, which is shown in FIG. 3B, for example. The user 8 can be a surgeon, for example. The pose detection device comprises at least one target 9 with at least one marker element 25 (see FIG. 4, for example) and at least one image capture device 10 for capturing the target. With the pose detection device, a pose of the target 9 relative to the image capture device can be determined, in particular in a coordinate system of the pose detection device. In this case, the target 9 includes at least one passive marker element 25, typically three passive marker elements 25.

FIG. 4 shows that the target 9 is fastened to the instrument 24. The instrument 24 can be configured as an aspirator, for example. The instrument 24 is in this case held by the user 8 in such a way that the target 9 is arranged in a capture region of the image capture device 10.

The pose of the instrument 24 can be detected by the pose detection device, by virtue of the pose of the target 9 being determined, in particular in image-based fashion, wherein the pose of the instrument 24 can then also be determined on account of the fixed arrangement of the target 9 on the instrument 24. A relative pose between target 9 and instrument 24 may be known in advance in this case and may be determined, for example, by registration.

Also shown is an image capture device 10 of the microscopy system 1, for example a CCD camera. This image capture device 10 is arranged in a microscope body 16 of the microscope 2. In particular, the image capture device is arranged in a housing of the microscope body 16. Moreover, the image capture device 10 is in particular arranged mechanically rigidly on a part of the microscope 2 and is thus arranged in a fixed position relative to said part.

Also shown is a signal connection and/or data connection 12 between the image capture device 10 and the control device 7. With the control device 7 or with an evaluation device (not shown), which may be part of the pose detection device for example, it is possible to determine a relative pose between target 9 and image capture device 10 in a three-dimensional coordinate system of the pose detection device. By way of example, it is possible to determine the pose of the target 9 in a two-dimensional image coordinate system of the image capture device 10 and then, on the basis of this pose, a pose in the coordinate system of the pose detection device. In this case, both a position and an orientation can be determined in the three-dimensional coordinate system of the pose detection device. By fastening the target 9 to the instrument 19, it is thus also possible to determine a pose of the instrument 19 in the coordinate system of the pose detection device and thus also in the reference coordinate system. In particular, a change in the pose of the target 9 and thus also a change in the pose of the instrument 19 can be detected with the pose detection device.

Before the microscopy system 1 is put into operation, the coordinate system of the pose detection device can be registered with the reference coordinate system shown. In other words, a transformation rule can be determined for transforming the pose in the coordinate system of the pose detection device into the reference coordinate system.

FIG. 4 shows that the image capture device 10 is arranged in the microscope body 16. Naturally, it is also possible to fasten these to the microscope body 16 outside of the latter. It is also possible not to fasten the image capture device to the microscopy system 1 but rather to a stand of the pose detection device, which differs from the stand 3 of the microscopy system 1.

The pose of the target 9 can be detected by evaluating exactly one two-dimensional image representation of the image capture device 10.

Also shown is a patient 13 lying on an operating table 14. Also shown is that the microscope 2 comprises an eyepiece 15 into which the user 8 looks in order to view, through the microscope 2, a partial region of the patient 13, in particular with magnification.

Also shown is an optical axis 17 of the microscope 2. In a beam direction along this optical axis from the microscope 2 to the patient 13, the image capture device 10 is arranged in front of a glass plate 18 of the microscope 2, which closes off the interior of the housing of the microscope body 16 from the external environment. The glass plate 18 is thus arranged between the image capture device 10 and the patient 13 who is to be observed.

A capture region of the image capture device 10 for pose detection in this case at least partially overlaps with a capture region of the microscope for magnified depiction of the patient or of regions of the body of the patient 13.

By moving the instrument 24, for example with his hands, it is possible that the user 8 moves the target 9 and thus changes the pose of the latter. The change in pose can be detected in this case by the pose detection device, with a pose set in this way then being able to be determined as the pose of a reference surface point 22 (see FIG. 3B).

Angle sensors for detecting a relative pose between the movable parts of the stand 3 are not shown, with the control device 7 being able to determine a spatial pose of the microscope 2, in particular also of the optical axis 17, on the basis of output signals from the angle sensors.

The microscopy system is operable with the control device 7, in such a way that the microscope 2 moves at a constant distance A (see FIG. 3a) around a pivot point 21, the pivot point 21 being an intersection of the optical axis 17 of the microscope 2 and a reference surface 19.

Further, the reference surface 19 can be determined on the basis of data, in particular with the control device 7. This has already been explained above.

LIST OF REFERENCE NUMERALS

1 Microscopy system
2 Microscope
3 Stand
4 Axis of rotation
5 Axis of rotation
6 Axis of rotation 7 Control device
8 User
9 Target
10 Image capture device
12 Signal connection and/or data connection
13 Patient
14 Operating table
15 Eyepiece
16 Microscope body
17 Optical axis
18 Glass plate
19 Instrument
20 Situs opening
21 Pivot point
22 Reference surface point
23 Cavity
24 Pose marking instrument
25 Marker element
26 Focal point
A Distance
S1 First step
S2 Second step
S2a First partial step
S2b Second partial step
S3 Third step
S4 Fourth step

What is claimed is:

1. A method for operating a microscopy system, the method comprising:
defining a pivot point as an intersection between an optical axis of a microscope of the microscopy system and a reference surface;
operating the microscopy system such that the microscope of the microscopy system moves around the pivot point;
determining a pose of the reference surface in a focal position-independent reference coordinate system independently of a focal position of the microscope; and
storing information about the pose of the reference surface in a retrievable form in a memory,
retrieving the information about the pose of the reference surface to determine the pivot point after a change in a pose of the optical axis of the microscope of the microscopy system, and
wherein the pivot point is determined as the intersection between the optical axis in a current pose and the reference surface defined by the stored information.

2. The method as claimed in claim 1, wherein the pose of the reference surface is defined in an object plane-independent reference coordinate system.

3. The method as claimed in claim 2, wherein the reference surface is determined by defining at least one reference surface point, with the reference surface being defined as or being arranged in a plane which is oriented perpendicular to the optical axis of the microscope and in which the reference surface point is arranged.

4. The method as claimed in claim 3, wherein the at least one reference surface point is determined as a focal point set by a user, or
wherein the at least one reference surface point is defined by a positioning of a pose marking instrument, or
wherein the at least one reference surface point is determined based on a position and/or orientation of at least one marker, or
wherein the at least one reference surface point is defined based on a viewing direction detection.

5. The method as claimed in claim 3, wherein the pose of a reference surface point is defined by changing the pose of an already defined reference surface point.

6. The method as claimed in claim 1, wherein the pose and/or a shape of the reference surface is defined such that an area encompassed by a situs opening forms the reference surface or is at least partially encompassed by the reference surface.

7. The method as claimed in claim 6, wherein the situs opening is defined automatically or manually.

8. The method as claimed in claim 1, wherein topographical information of a situs is determined, the pose and/or a shape of the reference surface being determined based on this topographical information.

9. The method as claimed in claim 1, wherein the focal position is changed based on a change in a distance of the microscope from the pivot point.

10. A microscopy system, comprising:
a microscope;
a stand for holding the microscope; and
a controller configured to control the microscopy system,
wherein the microscopy system is operable such that the microscope moves around a pivot point defined as an intersection between an optical axis of the microscope and a reference surface,
wherein a pose of the reference surface is determined in a focal position-independent reference coordinate independently of a focal position of the microscope,
wherein information about the pose of the reference surface is stored in a retrievable form in a memory,
wherein the information about the pose of the reference surface is retrieved to determine the pivot point after a change in a pose of the optical axis of the microscope, and
wherein the pivot point is determined as the intersection between the optical axis in a current pose and the reference surface defined by the stored information.

11. The microscopy system as claimed in claim 10, wherein the pose of the reference surface is defined in an object plane-independent reference coordinate system.

12. The microscopy system as claimed in claim 10, wherein the microscopy system comprises a device for generating topographical information and/or at least one pose detection device for detecting a pose of a pose marking instrument and/or a marker.

* * * * *